(12) United States Patent
Van Weerd

(10) Patent No.: US 12,194,146 B2
(45) Date of Patent: Jan. 14, 2025

(54) LIPID-BASED COATING COMPOSITION, AND AN OBJECT HAVING A LIPID-BASED COATING

(71) Applicant: LIPOCOAT B.V., Enschede (NL)

(72) Inventor: Jasper Van Weerd, Enschede (NL)

(73) Assignee: Lipocoat IP Holding B.V., Enschede (NL)

( * ) Notice: Subject to any disclaimer, the term of this patent is extended or adjusted under 35 U.S.C. 154(b) by 1038 days.

(21) Appl. No.: 16/975,826

(22) PCT Filed: Feb. 26, 2019

(86) PCT No.: PCT/EP2019/054714
§ 371 (c)(1),
(2) Date: Aug. 26, 2020

(87) PCT Pub. No.: WO2019/166424
PCT Pub. Date: Sep. 6, 2019

(65) Prior Publication Data
US 2020/0405641 A1  Dec. 31, 2020

(30) Foreign Application Priority Data
Feb. 27, 2018  (EP) .................................... 18158897

(51) Int. Cl.
*A61K 9/127* (2006.01)
*A61L 27/16* (2006.01)
*B29D 11/00* (2006.01)

(52) U.S. Cl.
CPC ............ *A61K 9/1271* (2013.01); *A61L 27/16* (2013.01); *B29D 11/00038* (2013.01); *B29D 11/00865* (2013.01)

(58) Field of Classification Search
CPC . A61K 9/1271; A61L 27/16; B29D 11/00038; B29D 11/00865
See application file for complete search history.

(56) References Cited

U.S. PATENT DOCUMENTS

2008/0241942 A1  10/2008  Zhu et al.
2016/0015862 A1*  1/2016  Ahlering ................. A61L 29/06
                                                        604/103.02

FOREIGN PATENT DOCUMENTS

| CN | 101134017 A | 3/2008 |
|---|---|---|
| CN | 107106692 A | 8/2017 |
| EP | 3093661 A1 | 11/2016 |
| JP | 2017524467 A | 8/2017 |
| WO | 01/15752 A1 | 3/2001 |
| WO | 01/58910 A2 | 8/2001 |
| WO | 2014/184383 A1 | 11/2014 |
| WO | 2015/193887 A1 | 12/2015 |

OTHER PUBLICATIONS

Zhang, Y. et al., PEGylated Phospholipid Membrane on Polymer Cushion and Its Interaction with Cholesterol, Langmuir, 2010. vol. 26, No. 13, pp. 111410-11144.*
Japanese Office Action dated Oct. 4, 2022 for family member Application No. JP20200567637.
Chinese Office Action dated Mar. 18, 2022 for family member Application No. 201980015634.5.
Arouri, A. et al., Phospholipase A2-Susceptible Liposomes of Anticancer Double Lipid-Prodrugs, European Journal of Pharmaceutical Sciences, 2012, vol. 45, No. 4, pp. 408-420.
Crielaard, B.J. et al., An in vitro assay based on surface plasmon resonance to predict the in vivo circulation kinetics of liposomes, Journal of Controlled Release, Jul. 2011, vol. 156, No. 3, pp. 307-314, Elsevier, Amsterdam, NL.
Zhang, Y. et al., PEGlyated Phospholipid Membrane on Polymer Cushion and Its Interaction with Cholesterol, Langmuir, 2010, vol. 26, No. 13, pp. 11140-11144.
Linden, M.V., Stabilization of Phospholipid Coatings in Capillary Electrophoresis, Oct. 24, 2008, XP055483153, Retrieved from the Internet: URL:https://helda.helsinki.fi/bitstream/handle/10138/21125/stabiliz.pd?sequence=1.
Sindt, C.W., Tangible Hydra-PEG: A Novel Custom Contact Lens Coating Technology Designed to Improve Patient Comfort and Satisfaction, Jan. 1, 2016, XP055483351, Retrieved from the Internet: URL:https://www.artoptical.com/storage/docs/THP_White_Paper.pdf., the whole document.
Van Weerd, J., Novel Biomedical Applications of Supported Lipid Bilayers, PhD Thesis, Jan. 16, 2015, XP55482572, Retrieved from the Internet: URL:https://ris.utwente.nl/ws/portalfiles/portal/6054385, the whole document.
Castellana, E.T. et al., Solid Supported Lipid Bilayers: From Biophysical Studies to Sensor Design, Surface Science Report, 2006, vol. 61, No. 10, pp. 429-444.

* cited by examiner

*Primary Examiner* — Genevieve S Alley
(74) *Attorney, Agent, or Firm* — Hudak, Shunk & Farine Co. LPA

(57) ABSTRACT

A lipid-based coating composition for coating a medical device, wherein the coating composition includes a) lipid vesicles consisting of i. 85-95 mol % of a phospholipid (A) having a phosphatidylcholine group; ii. 5-12 mol % of a PEGylated phospholipid (B); optionally 0-3 mol % of a lipophilic compound (C) other than lipids (A) and (B); b) 0-5 wt. % of a water-soluble additive (D); and c) at least 95 wt. % of water, wherein lipid vesicles having a number average size between 50 and 140 nm (measured according to dynamic light scattering) and wherein the lipid vesicle concentration ranges between 0.025 mg/ml and 2 mg/ml, and wherein the mol % of lipids (A), (B) and (C) is calculated relative to the total molar amount of lipids (A)+(B)+(C) in the lipid-based coating composition and wherein the wt. % of water-soluble additive (D) is calculated relative to the weight of the total composition.

15 Claims, 11 Drawing Sheets

Experiment 1

Mn 94.80 ± 31.00

Experiment 2

Mn 74.80 ± 27.37

Experiment 3

Mn 51.90 ± 18.23

Experiment 4

Mn 17.11 ± 4.62

| | Experiment 1 | Experiment 2 | Experiment 3 | Experiment 4 |
|---|---|---|---|---|
| Before dehydration | Coverage 100%<br>Lipid coating formation | Coverage 100%<br>Lipid coating formation | Coverage 100%<br>Lipid coating formation | Coverage 0%<br>No lipid coating formation |
| After dehydration | Coverage 50%<br>Degradation | Coverage 100%<br>No degradation | Coverage 100%<br>No degradation | Coverage 0%<br>N.A. |

Fig. 4

LIPID-BASED COATING COMPOSITION, AND AN OBJECT HAVING A LIPID-BASED COATING

FIELD OF THE INVENTION

The present invention relates to the use of a lipid-based coating composition, medical devices (such as contact lenses, catheters and medical implants) treated with the coating composition and medical devices having a lipid-based coating.

BACKGROUND OF THE INVENTION

Coating of substrates is known in the art. In general, coatings are coverings that can be applied to a surface or an object. Coatings can be for example decorative, functional or both. Decorative coatings include for example paints and or lacquers. Functional coatings include for example adhesive, optical, catalytic, light sensitive, magnetic, electrical, conductive, insulating, scent properties and or protective. Functional (protective) coatings include for example anti-corrosion, anti-scratch, waterproof, anti-microbial, anti-inflammatory, anti-fouling, anti-thrombogenic, lubricious and/or bio-active. The typical lipid-based coating, not limited to, Supported Lipid Bilayers are commonly applied using vesicles of varying size and composition. SLBs are generally prepared via vesicle fusion and have been widely used in research since they were first reported (McConnel and Tamm 1985). SLBs have shown great promise as an anti-fouling surface and as tunable coatings since their surface composition and function can be altered. The anti-fouling nature of SLBs and their tunable composition makes them an ideal candidate to serve as a surface coating on solid materials where properties such as anti-fouling, wetting, lubricity and bio-functionality are exploited.

Improper wetting, low lubricity and high fouling is a known problem in healthcare and with the use of medical devices.

EP 3 093 661 describes an artificial cell membrane comprising a lipid bilayer. The membrane is used to study interactions between molecules in a liquid environment as an analysis device.

Medical devices are prepared from biomaterials, natural or synthetic materials (metal or polymer) that are suitable for tissue contact or contact with biological fluids. Medical devices tend to lack proper control over surface properties resulting in unwanted phenomena occurring on the medical device or biomaterial interface such as improper wetting, low lubricity and fouling of proteins, cells and micro-organisms. This can be the case on first use or change during the use time of the device. As a result, comfort, safety and performance of the medical device can be affected. For example, more than half of the contact lens users experience discomfort that can be related to improper contact lens wetting and to low lubricity. In some cases, this is affected by protein fouling on the lens surface. Generally, wetting and lubricity are important surface properties for medical devices that enter body orifices or frequently move across a tissue interface. In addition, fouling of micro-organisms on the lens surface increases the risk for eye infection—nowadays 1 in 500 contact lens users develops an eye infection. Fouling of micro-organisms on more invasive devices pose a high health care risk. Half of all the infections that strike inpatients, so-called health care associated infections, are caused by bacteria fouling of catheters. Resulting in increased hospital stay, increased health care costs and deaths. Similar to contact lenses, with catheters—as they move through a body orifice—there is a need to also increase surface wetting and lubricity for comfortable insertion and removal of the device without tissue damage. Additionally, the propensity to adsorb proteins (protein fouling) often results in a coagulation response when in contact with blood. For blood contacting devices such as cardiovascular catheters, blood coagulation is undesired and anti-thrombogenic properties are required. Also, medical implants, such as orthopedic implants, are affected by fouling of micro-organisms. Although the risk is generally considered low (<2%), bacteria fouling and the resulting infection in most cases require revision surgery during which the implant is removed, tissue is cleared, and a new device is placed back in the patient.

A contact lens is a thin lens placed directly on the surface of the eye and can be classified by their primary function, their material, wear and replacement schedule. Based on the primary function, contact lenses are known that correct vision—most commonly by correcting refractive error. Cosmetic contact lenses are designed to change the appearance of the eye but can also correct refractive error. Therapeutic contact lenses are known, which are used in the treatment and management of non-refractive disorders of the eye.

Contact lenses are usually either soft, rigid or hybrid. Examples of soft contact lenses are hydrogel and silicon hydrogel contact lenses, Examples of rigid contact lenses are rigid gas permeable contact lenses. Examples of hybrid contact lenses are lenses which combine soft and rigid materials.

Contact lenses can be used for different periods of time, for example use during the day, use during the night or overnight—in the case of extended wear lenses.

Furthermore, contact lenses can have different replacement intervals, for example they can be discarded daily (daily disposable lenses), every two weeks, every few months or every half year or longer (mostly the case for rigid gas permeable contact lenses). A special class of rigid lenses, the so-called Ortho K lenses, are only worn during the night to correct vision during the day. Most contact lens types, with the exception of daily disposable lenses, require the use of lens care products for cleaning and storage.

A catheter is a thin tube that can be inserted in the body to treat diseases, for diagnostic purposes or perform a surgical procedure. By modifying the material or adjusting the way catheters are manufactured, it is possible to tailor catheters for different applications like for example cardiovascular, urological, gastrointestinal, neurovascular and ophthalmic applications.

Implants are manufactured to replace a missing biological structure, support a damaged biological structure, or enhance an existing biological structure. In some cases, implants contain electronics e.g. artificial pacemaker and cochlear implants. Some implants are bioactive, such as subcutaneous drug delivery devices in the form of implantable pills or drug-eluting stents.

Implants can roughly be categorized into groups by application, for example sensory and neurological, cardiovascular, orthopedic, contraception, cosmetic and other organs and systems.

To control the inherent medical device or biomaterial surface properties and match them with the application requirements, coatings and new materials are studied. In the art, medical device surface coatings are used to improve the performance of said medical devices and e.g. reduce (bio) fouling. These include commercially available coatings such as ComfortCoat® (DSM) for use on catheters and Tangible Hydra-PEG™ (Contamac) for use on contact lenses.

Although performance can be improved with the current coatings, many end-users still suffer from complications. For example, despite advances made in contact lens materials (such as PC Technology™, CooperVision) and contact lens surface treatments such as the HydraPEG™ coating, a large group of contact lens users still experience discomfort and safety risks due to fouling of the contact lens surface with proteins and or micro-organisms, improper fit and a lack of (sustained) wetting. Similarly, despite new catheter materials and coatings, health care associated infections are still primarily caused by contaminated catheters. Therefore, there is a need to further improve and tailor medical device surface properties. In addition to medical device applications, food, pharma, maritime and consumer products could benefit from the present invention.

SUMMARY OF THE INVENTION

The present invention relates to the use of a lipid-based coating composition for coating a medical device, wherein the coating composition comprises
  a) Lipid vesicles consisting of
    i. 85-95 mol % of a phospholipid (A) having a phosphatidylcholine group;
    ii. 5-12 mol % of a PEGylated phospholipid (B);
    iii, optionally 0-3 mol % of a lipophilic compound (C) other than lipids (A) and (B);
  b) 0-5 wt. % of a water-soluble additive (D); and
  c) at least 95 wt. % of water,
wherein lipid vesicles having a number average size between 50 and 140 nm (measured according to dynamic light scattering) and
wherein the lipid vesicle concentration ranges between 0.025 mg/ml and 2 mg/ml, and
wherein the mol % of lipids (A), (B) and (C) is calculated relative to the total molar amount of lipids (A)+(B)+(C) in the lipid-based coating composition, wherein the wt. % of water-soluble additive D is calculated relative to the weight of the total composition and wherein the medical device is chosen from a contact lens, a catheter and medical implant.

The lipid-based coating composition can be applied to the surface of the medical device generating a coating consisting of
  I. 85-95 mol % of a phospholipid (A) having a phosphatidylcholine group;
  II. 5-12 mol % of a PEGylated phospholipid (B);
  III. Optionally 0-3 mol % of a lipophilic compound (C) other than lipids (A) and (B).
wherein the mol % of lipids (A), (B) and (C) are calculated relative to the amount of lipids (A)+(B)+(C) in the coating.

It has surprisingly been found that the coating as defined above is air-stable, and shows improved surface properties: the lipid-based coating can be used to improve surface wetting and lubricity and tailored to reduce fouling of proteins and micro-organisms.

Alternatively, the coating can be tuned to include bioactivity. In all cases the lipid-based coating can be used in conjunction with a supplement comprising the lipid-based coating composition that maintains the coating quality.

BRIEF DESCRIPTION OF THE DRAWINGS

FIG. 4 shows fluorescent microscopy analysis of experiments 1-4 in the formation of a lipid-coating, before and after drying of a coating on substrate

DETAILED DESCRIPTION OF THE INVENTION

Figure 1:
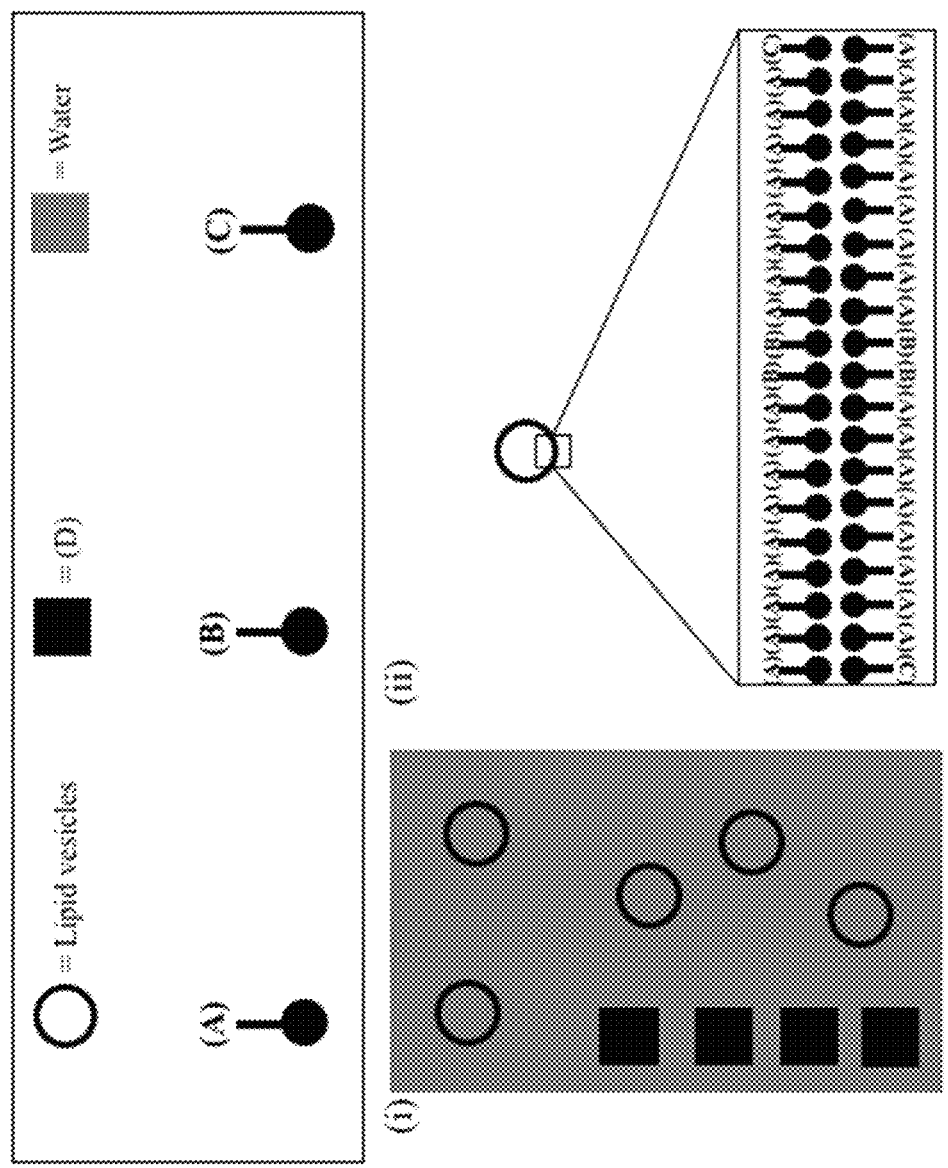
FIG. 1 shows schematically a lipid-coating composition containing lipid vesicles comprising of (A)+(B) and optionally (C).
Figure 2:
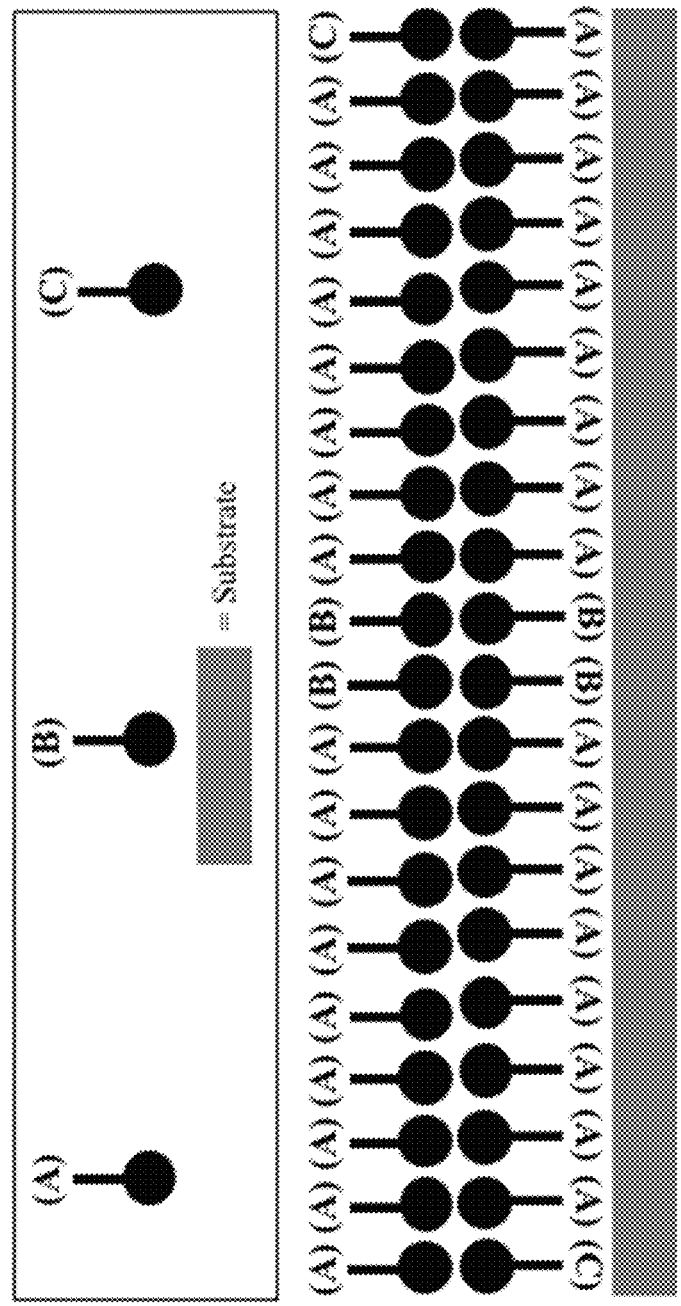
FIG. 2 shows the coating on a substrate, wherein the coating is a lipid bilayer comprising (A), (B) and (C).

The present invention relates to the use of a lipid-based coating composition for coating a medical device, wherein the coating composition comprises
  a) Lipid vesicles consisting of
    i. 85-95 mol % of a phospholipid (A) having a phosphatidylcholine group;
    ii. 5-12 mol % of a PEGylated phospholipid (B);
    iii. optionally 0-3 mol % of a lipophilic compound (C) other than lipids (A) and (B);
  b) 0-5 wt. % of a water-soluble additive (D); and
  c) at least 95 wt. % of water,
wherein lipid vesicles having a number average size between 50 and 140 nm (measured according to dynamic light scattering) and
wherein the lipid vesicle concentration ranges between 0.025 mg/ml and 2 mg/ml, and
wherein the mol % of lipids (A), (B) and lipophilic compound (C) are calculated relative to the amount of (A)+(B)+(C) in the lipid-based coating composition, and wherein the amount of water-soluble additive (D) and water is calculated relative to the total weight of the lipid-based coating composition.

The medical device is preferably selected from contact lenses, catheters and medical implants, more preferably from contact lenses and catheters, most preferably the medical device is a contact Jens.

Phospholipids in general have a hydrophilic head and two hydrophobic tails each. When phospholipids are exposed to water, they arrange themselves into e.g. a two-layered sheet (a bilayer) with all of their tails pointing towards the center of the sheet or as micelles with their tails pointing towards each other. The centers of this bilayer and micelle are non-polar and therefore contain almost no water and exclude molecules that dissolve in water but not in oil.

At a given temperature a lipid bilayer can exist in either a liquid or a gel (solid) phase. All lipids have a characteristic temperature at which they transition (melt) from the gel to the liquid phase—the phase transition temperature. In both phases the lipid molecules are mostly prevented from flip-flopping across the bilayer, but in liquid phase bilayers a given lipid will exchange locations with its neighbor millions of times a second. Unlike liquid phase bilayers, the lipids in a gel phase bilayer are locked in place with very limited mobility.

While lipid tails primarily modulate bilayer phase behavior, it is the head group of the lipid that determines the bilayer surface chemistry. Of the phospholipids, the most common head group is phosphatidylcholine (PC). Phosphatidylcholine is a zwitterionic head group, as it has a negative charge on the phosphate group and a positive charge on the choline but, because these local charges balance, no net charge is present at physiological pH. Another example of a head group with no net charge at physiological pH is phosphatidylethanolamine.

Other head groups, such as for example, phosphatidic acid, phosphatidylserine and phosphatidyl glycerol carry a negative charge at physiological pH.

Due to their zwitterionic nature, phosphatidylcholine derivatives are preferably used for coating applications; phosphatidylcholine derivatives are a class of lipids that bear a phosphatidylcholine headgroup and can have natural or synthetic hydrophobic tails of varying length and composition such as degree of saturation. Examples of natural hydrophobic tails are palmitoyl, oleoyl, diphytanoyl and myristoyl. Examples of synthetic hydrophobic tails are diacetylenic and acrylate containing tails.

The phospholipids (A) contain a phosphatidylcholine (PC) head group is.

Examples of phospholipids (A) are 1,2-didecanoyl-sn-glycero-3-phosphocholine (DDPC), 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine(DSPC), 1,2-Dioleoyl-sn-glycero-3-phosphocholine (DOPC), 1-palmitoyl-2-oleoyl-sn-glycero-3-phosphocholine (POPC), 1,2-dierucoyl-sn-glycero-3-phosphocholine (DEPC), DiynePC lipids such as 1,2-bis(10,12-tricosadiynoyl)-sn-glycero-3-phosphocholine and 1-palmitoyl-2-(10,12-tricosadiynoyl)-sn-glycero-3-phosphocholine. Preferred phospholipids (A) are chosen from the group consisting of 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-phosphocholine (DOPC), 1-palmitoyl-2-oleoyl-sn-glycero-3-phosphocholine (POPC). More preferably the phospholipids are chosen from the group consisting of 1,2-dipalmitoyl-sn-glycero-3-phosphocholine (DPPC) and 1,2-dioleoyl-sn-glycero-3-phosphocholine (DOPC).

Examples of PEGylated phospholipids (B) are saturated and unsaturated (e.g. 14:0, 16:0, 18:0 and 18:1) phosphatidylethanolamine derivatives conjugated to polyethylene glycol (PEG). The PEG group in the PEGylated phospholipids have preferably a Mw of 200-10,000. The Mw of the PEG group is preferably between 300 and 6000 daltons, more preferably between 500 and 4000 daltons. In this range, the balance between stability of the composition and ability to coat a substrate is optimal: at higher PEG Mw, the stability of the coating composition increases, but the ability to coat a substrate with this composition decreases. At lower PEG Mw, the stability of the coating composition maybe insufficient. In addition, the PEG Mw could affect properties such as wetting and lubricity. Preferably, PEGylated phospholipids B are chosen from the group consisting of 1,2-distearoyl-sn-glycero-3-phosphoethanolamine-N-[methoxy(polyethylene glycol)-350] (DSPE-PEG350), 1,2-distearoyl-sn-glycero-3-phosphoethanolamine-N-[methoxy(polyethylene glycol)-550] (DSPE-PEG550), 1,2-distearoyl-sn-glycero-3-phosphoethanolamine-N-[methoxy(polyethylene glycol)-750] (DSPE-PEG750), 1,2-distearoyl-sn-glycero-3-phosphoethanolamine-N-[methoxy(polyethylene glycol)-1000] (DSPE-PEG1000), 1,2-distearoyl-sn-glycero-3-phosphoethanolamine-N-[methoxy(polyethylene glycol)-2000] (DSPE-PEG2000), 1,2-distearoyl-sn-glycero-3-phosphoethanolamine-N-[methoxy(polyethylene glycol)-3000] (DSPE-PEG3000), 1,2-distearoyl-sn-glycero-3-phosphoethanolamine-N-[methoxy(polyethylene glycol)-5000] (DSPE-PEG5000), 1,2-dioleoyl-sn-glycero-3-phosphoethanolamine-N-[methoxy(polyethylene glycol)-350] (DSPE-PEG350), 1,2-dioleoyl-sn-glycero-3-phosphoethanolamine-N-[methoxy(polyethylene glycol)-550] (DSPE-PEG550), 1,2-dioleoyl-sn-glycero-3-phosphoethanolamine-N-[methoxy(polyethylene glycol)-750] (DSPE-PEG750), 1,2-dioleoyl-sn-glycero-3-phosphoethanolamine-N-[methoxy(polyethylene glycol)-1000] (DSPE-PEG1000), 1,2-dioleoyl-sn-glycero-3-phosphoethanolamine-N-[methoxy(polyethylene glycol)-2000] (DSPE-PEG2000), 1,2-dioleoyl-sn-glycero-3-phosphoethanolamine-N-[methoxy(polyethylene glycol)-3000] (DSPE-PEG3000), 1,2-dioleoyl-sn-glycero-3-phosphoethanolamine-N-[methoxy(polyethylene glycol)-5000] (DSPE-PEG5000), 1,2-dipalmitoyl-sn-glycero-3-phosphoethanolamine-N-[methoxy(polyethylene glycol)-350] (DSPE-PEG350), 1,2-dipalmitoyl-sn-glycero-3-phosphoethanolamine-N-[methoxy(polyethylene glycol)-550] (DSPE-PEG550), 1,2-dipalmitoyl-sn-glycero-3-phosphoethanolamine-N-[methoxy(polyethylene glycol)-750] (DSPE-PEG750), 1,2-dipalmitoyl-sn-glycero-3-phosphoethanolamine-N-[methoxy(polyethylene glycol)-1000] (DSPE-PEG1000), 1,2-dipalmitoyl-sn-glycero-3-phosphoethanolamine-N-[methoxy(polyethylene glycol)-2000] (DSPE-PEG2000), 1,2-dioleoyl-sn-glycero-3-phosphoethanolamine-N-[methoxy(polyethylene glycol)-3000] (DSPE-PEG3000) and 1,2-dioleoyl-sn-glycero-3-phosphoethanolamine-N-[methoxy(polyethylene glycol)-5000] (DSPE-PEG5000). More preferably, PEGylated phospholipids B are chosen from the group consisting of 1,2-dipalmitoyl-sn-glycero-3-phosphoethanolamine-N-[methoxy(polyethylene glycol)-2000] (DPPE-PEG2000) and 1,2-dioleoyl-sn-glycero-3-phosphoethanolamine-N-[methoxy(polyethylene glycol)-2000] (DOPE-PEG2000).

In general, phospholipids comprise of a headgroup and one or more fatty acid tails. Examples of phospholipid headgroups include Phosphatidylcholine, Phosphatidic acid, Phosphatidylglycerol, Phosphatidylethanolamine and Phosphatidylserine. The fatty acid tail composition can vary in carbon chain length from 12 to 22 carbon atoms and can vary in degree of saturation wherein the C=C double bond can give either cis or trans isomers. Examples of saturated fatty acid tails include lauric acid, myristic acid, palmitic acid, stearic acid and behenic acid. Examples of unsaturated fatty acid tails include myristoleic acid, palmitoleic acid and oleic acid. Variations in fatty acid tail composition are jointly referred to as derivatives of a specific phospholipid headgroup.

Therefore, examples of phospholipids include Phosphatidylcholine derivatives, Phosphatidic acid derivatives, Phosphatidylglycerol derivatives, Phosphatidylethanolamine derivatives, Phosphatidylserine derivatives, Natural phospholipid derivatives, polyglycerin-phospholipids, functionalized-phospholipids, terminal activated-phospholipids, and PEGylated phospholipids.

Examples of Phosphatidic acid derivatives are 1,2-dimyristoyl-sn-glycero-3-phosphate (DMPA), 1,2-dipalmitoyl-sn-glycero-3-phosphate (DPPA), 1,2-distearoyl-sn-glycero-3-phosphate (DSPA).

Examples of Phosphatidylglycerol derivatives are 1,2-dimyristoyl-sn-glycero-3[Phospho-rac-(1-glycerol) (DMPG), 1,2-dipalmitoyl-sn-glycero-3[Phospho-rac-(1-glycerol) (DPPG), 1,2-distearoyl-sn-glycero-3[Phospho-rac-(1-glycerol) (DSPG), 1-almitoyl-2-oleoyl-sn-glycero-3 [Phospho-rac-(1-glycerol)] (POPG).

Examples of Phosphatidylethanolamine derivatives are 1,2-dimyristoyl-sn-glycero-3-phosphoethanolamine (DMPE), 1,2-dipalmitoyl-sn-glycero-3-phosphoethanolamine (DPPE), 1,2-distearoyl-sn-glycero-3-phosphoethanolamine (DSPE), 1,2-dioleoyl-sn-glycero-3-phosphoethanolamine (DOPE), DiynePE lipids such as 1,2-bis(10,12-tricosadiynoyl)-sn-glycero-3-phosphoethanolamine and 1-palmitoyl-2-(10,12-tricosadiynoyl)-sn-glycero-3-phosphoethanolamine, and conjugated phosphoethanolamines conjugated with, not limited to, peptides, proteins and fluorophores such as Texas Red-1,2-dihexadecanoyl-sn-Glycero-3-Phosphoethanolamine (TR-DHPE).

An example of Phosphatidylserine derivatives is for example 1,2-dioleoyl-sn-glycero-3-phosphoserine (DOPS), Examples of lipophilic compound (C) can be chosen from Phosphatidic acid derivatives, Phosphatidylglycerol derivatives, Phosphatidylethanolamine derivatives, Phosphatidylserine derivatives, natural phospholipid derivates, Sterols, cholesterol, desmosterol, lanosterol and derivatives of sterols, polyglycerin-phospholipids, functionalized-phospholipids, terminal activated-phospholipids), N-[1-(2,3-Dioleoyloxy)propyl]-N,N,N-trimethylammonium methylsulfate (DOTAP), proteins, peptides, amphiphiles, ionic polymers, sugar molecules, enzymes and pharmaceutical components. Derivatives can preferably be fatty acid tails, comprising between 12 and 22 Carbon atoms and can vary in degree of saturation wherein the C=C double bond can give either cis or trans isomers. Examples of saturated fatty acid tails include lauric acid, myristic acid, palmitic acid, stearic acid and behenic acid. Examples of unsaturated fatty acid tails include myristoleic acid, palmitoleic acid and oleic acid.

The concentration of lipid vesicles in the lipid-based coating composition comprising phospholipids (A), PEGylated phospholipids (B) and lipophilic compounds (C) is preferably between 0.025 mg/ml and 2 mg/ml, more preferably between 0.05 and 1.0 mg/ml. The number average size of lipid vesicles in the lipid-based coating composition is between 40-140 nm, preferably 80-120 nm as measured by dynamic light scattering.

Optionally, the lipid-based coating composition can also contain between 0-5 wt. % (relative to the total weight of the composition) of water-soluble additive (D) such as salts, buffers, (poly)electrolytes and complexing agents. Specific examples of water-soluble additives (D) are phosphate buffered saline (PBS), HEPES, $NaCl_2$ and $CaCl_2$. Preferably the amount of water-soluble additives ranges between 0 and 2 wt. %, or between 0 and 1 wt. %.

The lipid-based coating composition can be used to prepare a lipid coating on a substrate or used to repair defects in a lipid coating on a substrate.

The invention also relates the lipid-based coating composition that can be applied to a substrate generating a coating consisting of I. 85-95 mol % of a phospholipid (A) having a phosphatidylcholine group;
II. 5-12 mol % of a PEGylated phospholipid (B);
III. 0-3 mol % of a lipophilic compound (C) other than lipids (A) and (B).

wherein the mol % of lipids (A), (B) and lipophilic compound (C) are calculated relative to the amount of (A)+(B)+(C) in the lipid coating.

The lipid coating comprises at least phospholipid derivatives containing a phosphatidylcholine group and a phospholipid which is coupled to a polyethylene glycol (PEG) fragment. The lipid coating is prepared by coating an object with the lipid-based coating composition of the present invention. Application of a lipid coating is known in the art and can be applied using for example spin-coating, vesicle fusion and Langmuir-Blodgett.

More preferably, the lipid coating comprises between 90-95 mol % (of total lipid content) 1,2-dioleoyl-sn-glycero-3-phosphocholine (DOPC) and 5-10 mol % (of total lipid content) PEGylated phospholipid such as 1,2-dioleoyl-sn-glycero-3-phosphoethanolamine-N-[methoxy(polyethylene glycol)-2000] (DOPE-PEG2000).

The lipid coating can contain a lipid (C) other than phospholipid (A) and PEGylated phospholipid (B).

The lipid coating can be a monolayer, bilayer or multiplayer of phospholipid derivatives. Preferably the lipid coating is a bilayer. The material or object can be any suitable medical device or biomaterial for lipid coating formation or pretreated to allow for lipid coating formation such as described in US2008/0241942 and WO2014/184383.

The lipid coating of the object has the advantages of being anti-fouling, anti-thrombogenic, hydrophilic and lubricous, which is advantages for medical devices such as contact lenses and catheters and medical implants.

It is possible that the lipid coating abrases due to forces applied to the object and defects can occur in the lipid coating. It is possible to repair the coating by re-applying the lipid-based coating composition described before.

EXPERIMENTAL

Key in using a lipid-based coating for medical devices is having sufficient air-stability. Only then can the beneficial properties of lipid bilayers be exploited for the benefit of medical devices. Henceforth, a set of experiments has been performed to illustrate the importance of PEGylated phospholipid (B) in the present invention. Subsequently, experiments have been performed using the compositions of the present invention on medical devices thereby showing performance improvements after coating application.

Air-stability is defined by observing coating coverage before and after a dehydration step. In the event the difference between the pre and post dehydration is less than 5% in terms of coating coverage, the coating is deemed air-stable. In all other cases, the coating is deemed not air-stable. Observation of coating coverage can be achieved through addition of a lipophilic compounds (C) such as TR-DHPE.

Experiment 1 (Comparative)

Figure 3A:
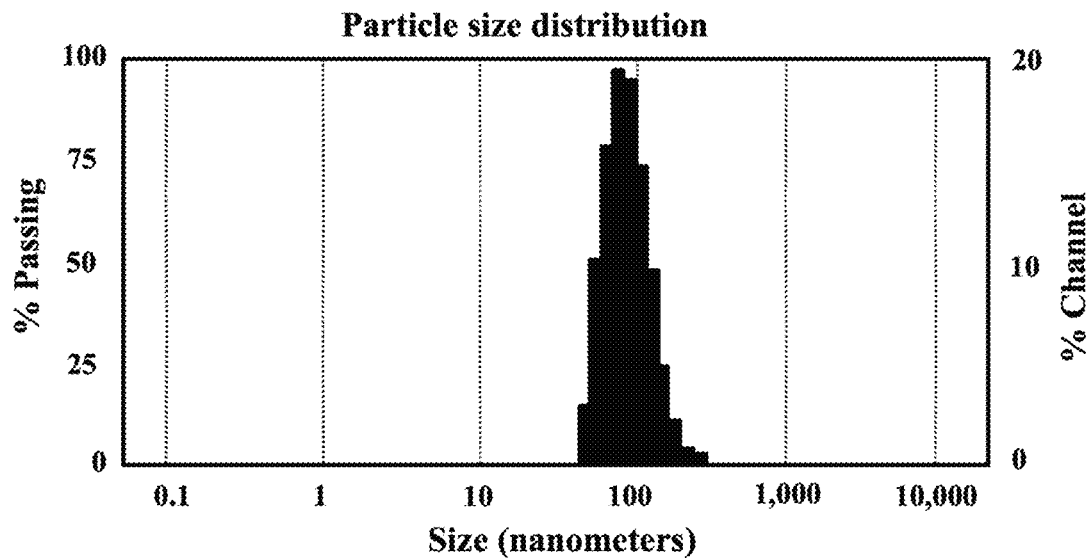
FIG. 3a-3d show size distributions of experiments 1-4 of lipid vesicles in dispersion

Experiment 1 was performed to evaluate the formation of lipid vesicles in the lipid coating composition using 0 mol % of PEGylated lipid (B). To this end, 99.8 mol % of total lipid content of lipid (A) DOPC (Avanti polar lipids), 0 mol % of total lipid content of PEGylated lipid (B) DSPE-PEG2000 (Avanti polar lipids) and 0.2 mol % of total lipid content of lipophilic compound (C) TR-DHPE (Thermo Fisher) in ethanol (ethanol absolute ≥99.8%, VWR) was prepared at a concentration of 50 mg/ml. The aforementioned concentrate solution was stored under argon at stored in microcentrifuge containers (VWR) at −20° C. for a maximum of 6 weeks. All lipids were ordered as powdered stocks and kept under argon atmosphere and stored at −20° C. for a maximum of 1 year. The concentrate solution was dispensed into 1 mL water containing water-soluble additive (D). The water-soluble additive (D) was 0.01 M HEPES (Sigma-Aldrich), 150 mM NaCl (Sigma-Aldrich) and 2 mM $CaCl_2$ pH (Sigma-Aldrich). The concentrate solution was dispensed within 1 second at a dilution factor of 200 using an air-displacement P10 micropipette (Eppendorf) and subsequently agitated using a table-top vortex (labdancer, VWR) and vortexed until steady-state. The resulting lipid-coating composition had a concentration of (A)+(B)+(C) of 0.25 mg/ml containing >95 wt. % water and was characterized using dynamic light scattering (DLS, Nanotrac wave, Microtrac). The mean number-weighted diameter (Mn) of the lipid vesicles was 94.80±31.00 nm and the solution appeared transparent by visual observation. Results shown in FIG. 3a.

Experiment 2

Figure 3B:
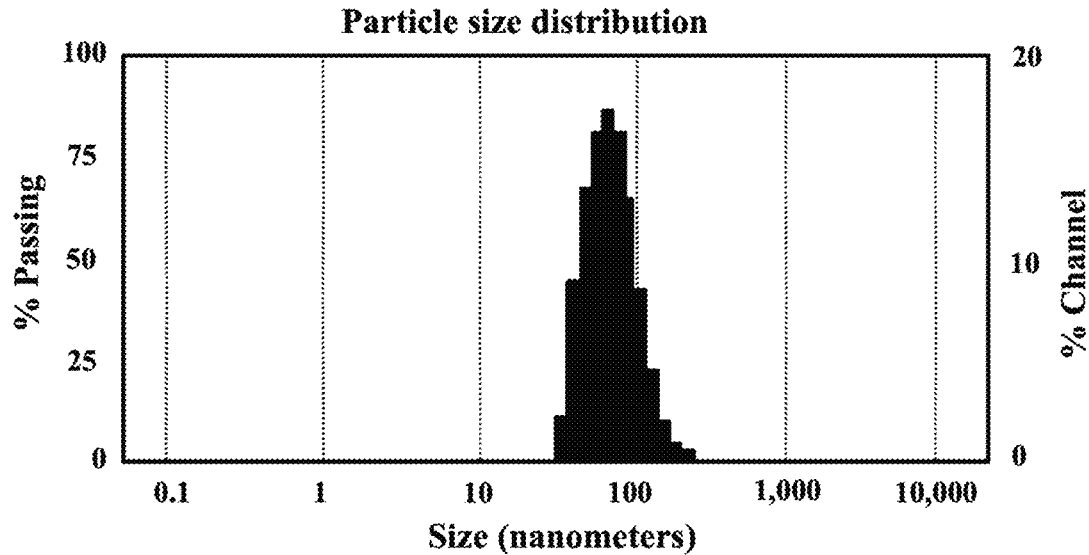

Experiment 2 was performed to evaluate the formation of lipid vesicles in the lipid coating composition using 5 mol % of PEGylated lipid (B). To this end, 94.8 mol % of total lipid content of lipid (A) DOPC (Avanti polar lipids), 5 mol % of total lipid content of PEGylated lipid (B) DSPE-PEG2000 (Avanti polar lipids) and 0.2 mol % of total lipid content of lipophilic compound (C) TR-DHPE (Thermo Fisher) in ethanol (ethanol absolute ≥99.8%, R) was prepared at a concentration of 50 mg/ml. The aforementioned concentrate solution was stored under argon at stored in microcentrifuge containers (VWR) at −20° C. for a maximum of 6 weeks. All lipids were ordered as powdered stocks and kept under argon atmosphere and stored at −20° C. for a maximum of 1 year. The concentrate solution was dispensed into 1 mL water containing water-soluble additive (D). The water-soluble additive (D) was 0.01 M HEPES (Sigma-Aldrich), 150 mM NaCl (Sigma-Aldrich) and 2 mM $CaCl_2$ pH (Sigma-Aldrich). The concentrate solution was dispensed within 1 second at a dilution factor of 200 using an air-displacement P10 micropipette (Eppendorf) and subsequently agitated using a table-top vortex (labdancer, VWR) and vortexed until steady-state. The resulting lipid-coating composition had a concentration of (A)+(B)+(C) of 0.25 mg/ml containing >95 wt. % water and was characterized using dynamic light scattering (DLS, Nanotrac wave, Microtrac). The mean number-weighted diameter (Mn) of the lipid vesicles was 74.80±27.37 nm and the solution appeared transparent by visual observation. Results shown in FIG. 3b.

Experiment 3

Figure 3C:
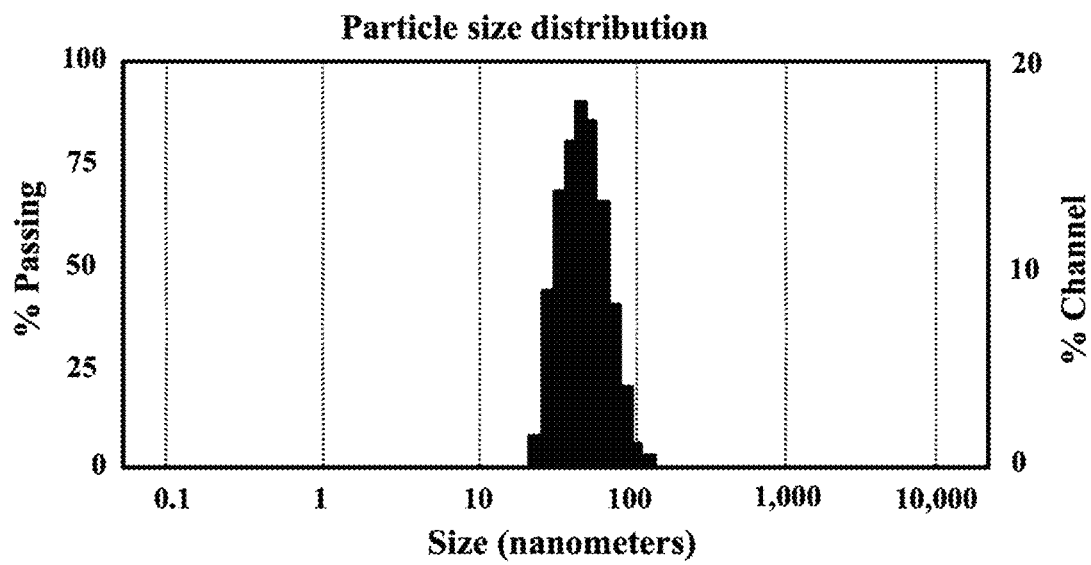

Experiment 3 was performed to evaluate the formation of lipid vesicles in the lipid coating composition using 10 mol % of PEGylated lipid (B). To this end, 89.8 mol % of total lipid content of lipid (A) DOPC (Avanti polar lipids), 10 mol % of total lipid content of PEGylated lipid (B) DSPE-PEG2000 (Avanti polar lipids) and 0.2 mol % of total lipid content of lipophilic compound (C) TR-DHPE (Thermo Fisher) in ethanol (ethanol absolute ≥99.8%, VWR) was prepared at a concentration of 50 mg/ml. The aforementioned concentrate solution was stored under argon at stored in microcentrifuge containers (VWR) at −20° C. for a maximum of 6 weeks. All lipids were ordered as powdered stocks and kept under argon atmosphere and stored at −20° C. for a maximum of 1 year. The concentrate solution was dispensed into 1 mL water containing water-soluble additive (D). The water-soluble additive (D) was 0.01 M HEPES (Sigma-Aldrich), 150 mM NaCl (Sigma-Aldrich) and 2 mM $CaCl_2$ pH (Sigma-Aldrich). The concentrate solution was dispensed within 1 second at a dilution factor of 200 using an air-displacement P10 micropipette (Eppendorf) and subsequently agitated using a table-top vortex (labdancer, VWR) and vortexed until steady-state. The resulting lipid-coating composition had a concentration of (A)+(B)+(C) of 0.25 mg/ml containing >95 wt. % water and was characterized using dynamic light scattering (DLS, Nanotrac wave, Microtrac). The mean number-weighted diameter (Mn) of the lipid vesicles was 51.90±18.23 nm and the solution appeared transparent by visual observation. Results shown in FIG. 3c.

Experiment 4 (Comparative)

Figure 3D:
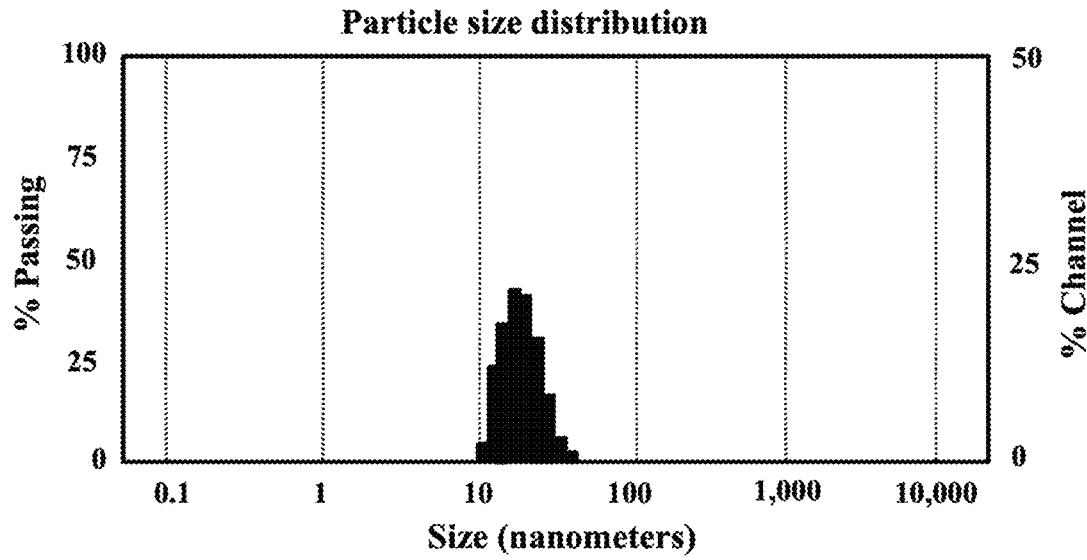

Experiment 4 was performed to evaluate the formation of lipid vesicles in the lipid coating composition using 20 mol % of PEGylated lipid (B). To this end, 79.8 mol % of total lipid content of lipid (A) DOPC (Avanti polar lipids), 20 mol % of total lipid content of PEGylated lipid (B) DSPE-PEG2000 (Avanti polar lipids) and 0.2 mol % of total lipid content of lipophilic compound (C) TR-DHPE (Thermo Fisher) in ethanol (ethanol absolute ≥99.8%, VWR) was prepared at a concentration of 50 mg/ml, The aforementioned concentrate solution was stored under argon at stored in microcentrifuge containers (VWR) at −20° C. for a maximum of 6 weeks. All lipids were ordered as powdered stocks and kept under argon atmosphere and stored at −20° C. for a maximum of 1 year. The concentrate solution was dispensed into 1 mL water containing water-soluble additive (D). The water-soluble additive (D) was 0.01 M HEPES (Sigma-Aldrich), 150 mM NaCl (Sigma-Aldrich) and 2 mM $CaCl_2$ pH (Sigma-Aldrich). The concentrate solution was dispensed within 1 second at a dilution factor of 200 using an air-displacement P10 micropipette (Eppendorf) and subsequently agitated using a table-top vortex (labdancer, VWR) and vortexed until steady-state. The resulting lipid-coating composition had a concentration of (A)+(B)+(C) of 0.25 mg/ml containing >95 wt. % water and was characterized using dynamic light scattering (DLS, Nanotrac wave, Microtrac). The mean number-weighted diameter (Mn) of the lipid vesicles was 17.11±4.62 nm and the solution appeared transparent by visual observation. Results shown in FIG. 3d.

Experiment 5

Experiment 5 was performed to evaluate lipid coating formation on control surfaces using the different lipid-coating compositions and their air-stability. To this end, 96-well glass bottoms plates (SensoPlates, Greiner Bio-one) were used. The 96-well glass bottoms plates were cleaned beforehand by incubation of 300 μL 2 v/v % Hellmanex III (Sigma-Aldrich) solution in milliQ for 1 hour at room temperature and subsequently rinsed with demi water to remove the detergent. 200 μL of lipid-coating compositions—prepared as described in experiment 1-4—was left to incubate for at least 5 minutes to form a lipid coating and subsequently washed with milliQ by means of serial dilution through addition of 100 μL of milliQ and removal of 100 μL of solution. At least 16 serial dilution were performed to remove remnants lipid-coating composition. The glass wells were characterized using fluorescence microscopy. To this end, an Olympus inverted IX71 epi-fluorescence research microscope with a Xenon X-cite 120PC as light source and a digital Olympus DR70 camera for image acquisition was used to acquire fluorescence micrographs. TR-DHPE was imaged using $510 \leq \lambda_{ex} \leq 550$ nm and $\lambda_{em} > 590$ nm. After imaging the samples were exposed to air to demonstrate air-stability, essential for commercial use. Results shown in FIG. 4. Successful lipid coating for formation was observed for experiment 1-3. Experiment 4 for did not show a successful coating formation most likely due to a lipid vesicles size distribution that not allows for coating formation by means of vesicle fusion. Only the lipid-based coating composition from experiment 2 and 3 showed improved stability.

Experiment 6

Figure 5:
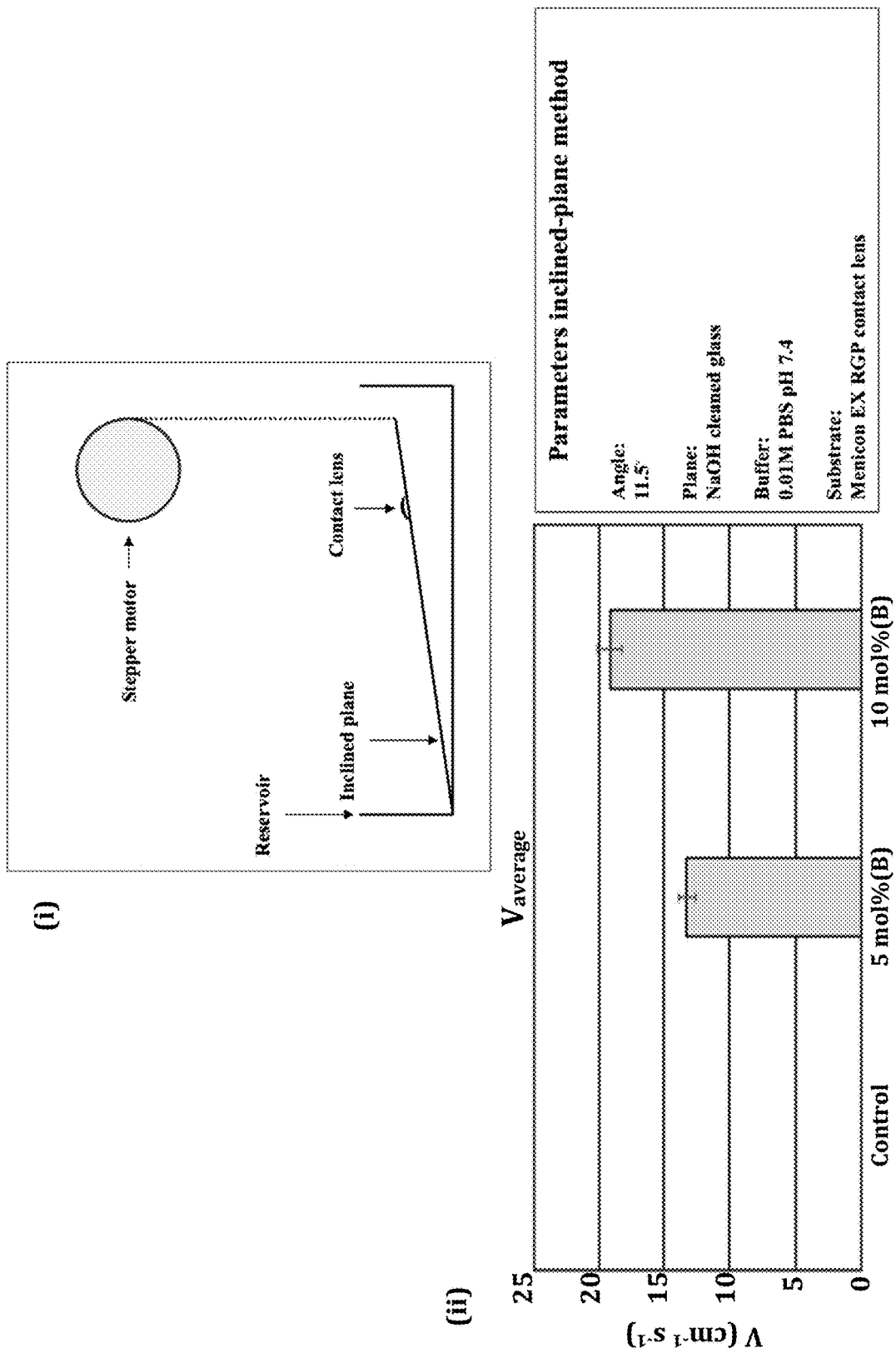
FIG. 5 shows a cross-sectional side view of the set-up for measuring lubricity of coatings on specific substrates and the test results of experiment 6.

Experiment 6 was performed to show the improved lubricity of coated RGP contact lenses using the lipid-coating composition resulting in a lipid coating on the contact lenses. To this end, 2 lipid-coating compositions were used as described in experiment 2 (5 mol % (B)) and experiment 3 (10 mol % (B)). Results shown in FIG. 5. Menicon EX contact lenses were used to illustrate improved lubricity using an inclined-plane method. Menicon EX lenses were cleaned with ethanol, dried and treated with oxygen plasma for 60 s at 40 watts (Plasma Prep II, SPI supplies). Control lenses were incubated in 0.01 M PBS buffer (Sigma-Aldrich). In addition, freshly treated Menicon EX lenses were incubated in lipid-coating composition 5 mol % (B) and 10 mol % (B) for 30 minutes and subsequently washed with 0.01 M PBS buffer (Sigma-Aldrich). Using an in-house build inclined-plane system (FIG. 5) lubricity improvement was shown. Here, the glass plane was cleaned in 0.1 M NaOH solution for 1 hour and rinsed with demi water. The cleaned glass plate was placed in a buffer reservoir containing 0.01 M PBS buffer (Sigma-Aldrich). One end of the glass plate was attached via a wire to a stepper motor to lift the glass plate and the angle was set at 11.5 degrees. This angle was chosen because no movement of the control Menicon EX lens was observed. Lenses were placed with the concave side facing the glass plate. A steel ferrule of 0.5 gram was added to the lenses while the lenses were kept in place using a tweezer. Once released, the speed of movement was deduced through movie analysis of the experiment using ImageJ software. Results are show demonstrate an increase in lubricity, as indicated by higher speeds, is correlated to higher mol % of (B) in the lipid-coating composition and therefore in the lipid coating on the lens.

Experiment 7

Figure 6:
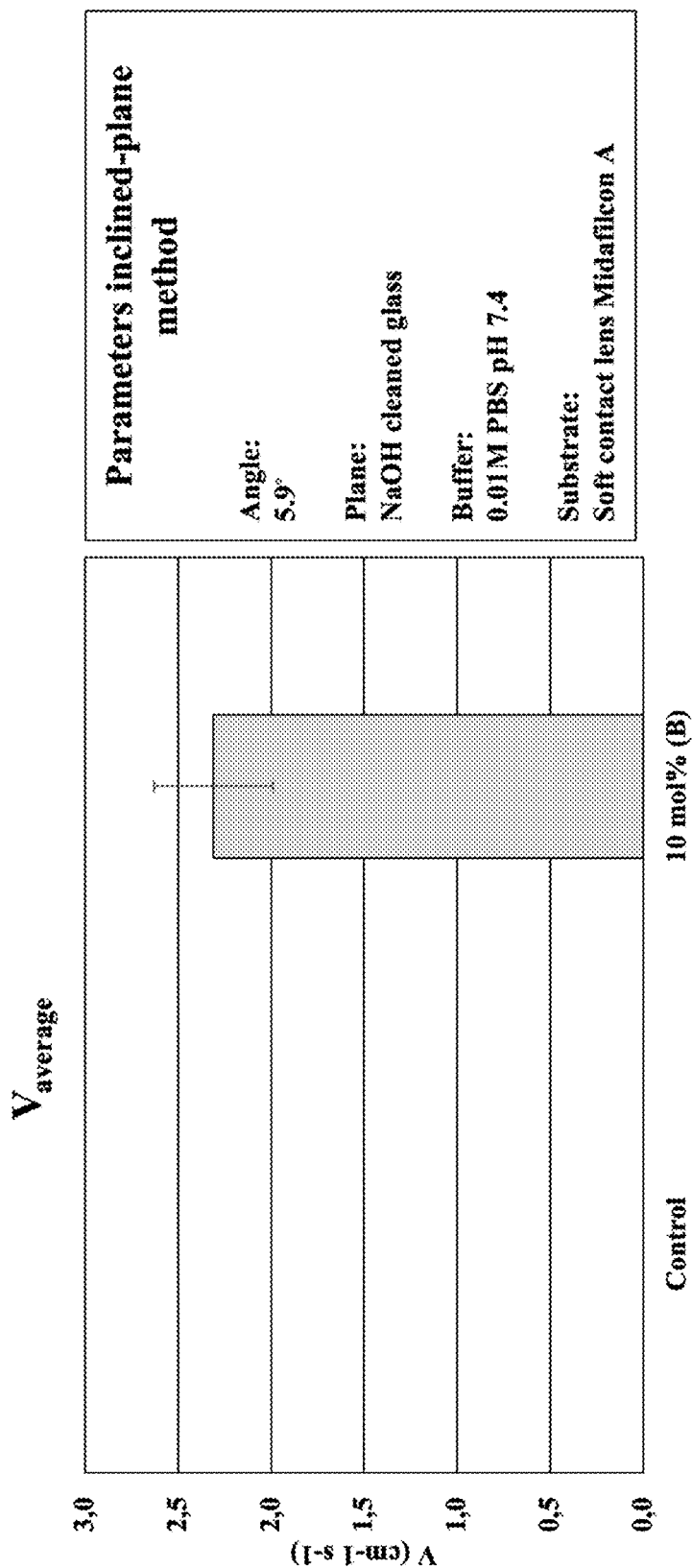
FIG. 6 shows lubricity test results according to experiment 7.

Experiment 7 was performed to show the improved lubricity of coated soft contact lenses using the lipid-coating composition resulting in a lipid coating on the contact lenses. To this end, the most lubricious composition from experiment 6 was used i.e. the lipid-coating compositions described in experiment 3 (10 mol % (B)). Results shown in FIG. 6. Midafilcon A contact lenses were used to illustrate improved lubricity using an inclined-plane method. Midafilcon A lenses were washed in milliQ, dried and treated with oxygen plasma for 60 s at 40 watts (Plasma Prep II, SPI supplies). Control lenses were incubated in 0.01 M PBS buffer (Sigma-Aldrich). In addition, freshly treated Midafilcon A lenses were incubated in lipid-coating composition 10 mol % (B) for 30 minutes and subsequently washed with 0.01 M PBS buffer (Sigma-Aldrich). Using an in-house build inclined-plane system (FIG. 5) lubricity improvement was shown. Here, the glass plane was cleaned in 0.1 M NaOH solution for 1 hour and rinsed with demi water. The cleaned glass plate was placed in a buffer reservoir containing 0.01 M PBS buffer (Sigma-Aldrich). One end of the glass plate was attached via a wire to a stepper motor to lift the glass plate and the angle was set at 5.9 degrees. This angle was chosen because no movement of the control Midafilcon A lens was observed. Lenses were placed with the concave side facing the glass plate. A steel ferrule of 0.5 gram was added to the lenses while the lenses were kept in place using a tweezer. Once released, the speed of movement was deduced through movie analysis of the experiment using ImageJ software. Results are show a similar trend compared to experiment 6 whereby highest speeds are observed with lipid-coating composition with 10 mol % (B).

Experiment 8

Figure 7:
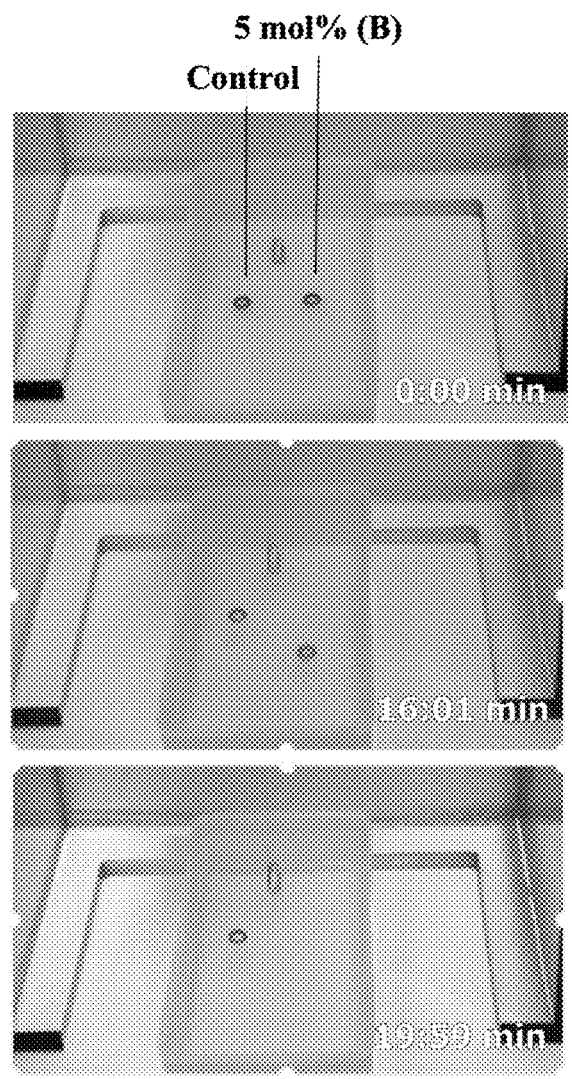
FIG. 7 shows lubricity test results according to experiment 8.

Experiment 8 was performed to show the improvement in lubricity of another type of coated rigid contact lenses using the lipid-coating composition resulting in a lipid coating on the contact lenses. To this end, a composition from experiment 2 was used i.e. the lipid-coating composition with 5 mol % (B). Results are shown in FIG. 7. UV1 contact lenses were used to illustrate improved lubricity using an inclined-plane method. UV1 lenses were washed in milliQ, dried and treated with oxygen plasma for 60 s at 40 watts (Plasma Prep II, SPI supplies). Control lenses were incubated in 0.01 M PBS buffer (Sigma-Aldrich). In addition, freshly treated UV1 lenses were incubated in lipid coating composition 5 mol % (B) for 30 minutes and subsequently washed with 0.01 M PBS buffer (Sigma-Aldrich). Using an in-house build inclined-plane system (FIG. 5) lubricity improvement was shown. Here, the glass plane was cleaned in 0.1 M NaOH solution for 1 hour and rinsed with demi water. The cleaned glass plate was placed in a buffer reservoir containing 0.01 M PBS buffer (Sigma-Aldrich). One end of the glass plate was attached via a wire to a stepper motor to lift the glass plate. Here, a dynamic lubricity analysis was performed wherein the stepper motor was used to lift the glass plate at one end in time thereby increasing the angle gradually. Lenses were placed with the concave side facing the glass plate at 0 degrees. A steel ferrule of 0.5 gram was added to the lenses while the lenses. Afterwards the glass plate was slowly lifted at one end using the stepper motor at a speed of 200 hz. The experiment was recorded, and movie analysis took place using ImageJ software. Results show a similar trend compared to experiment 6 and 7 whereby lenses coated with lipid-coating composition with 5 mol % (B) show mobility while the uncoated control lenses did not.

Experiment 9

Figure 8:
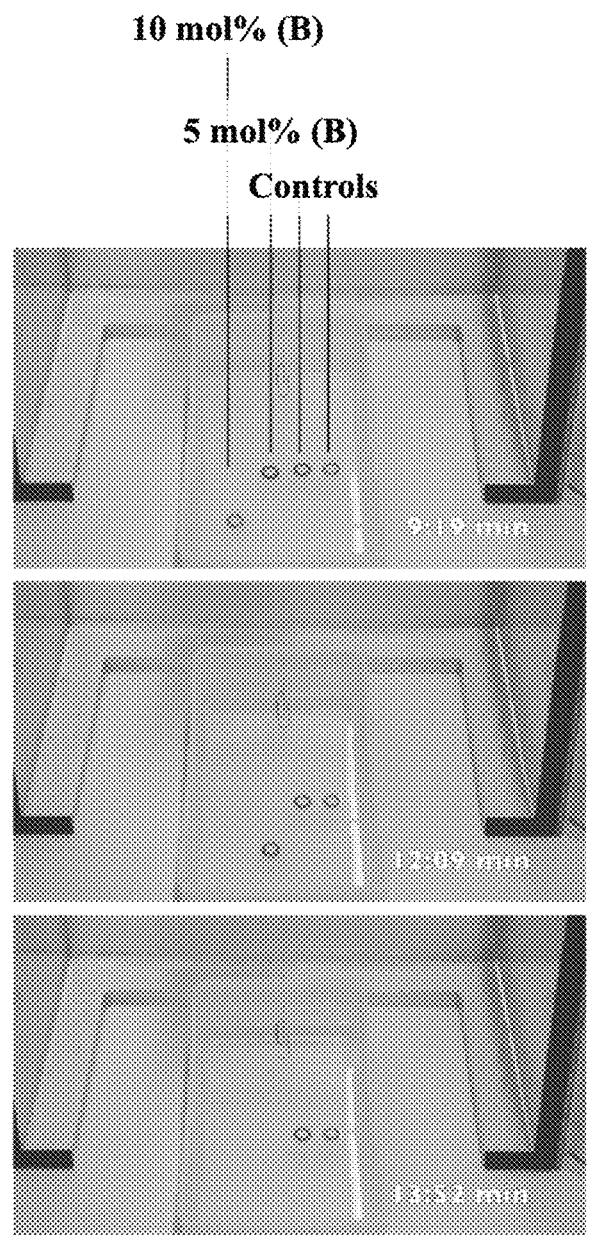
FIG. 8 shows lubricity test results according to experiment 9.

Experiment 9 was performed to show the improvement in lubricity of another type of coated soft contact lenses using the lipid-coating composition resulting in a lipid coating on the contact lenses. To this end, compositions from experiment 2 were used i.e. the lipid-coating composition with 5 and 10 mol % (B). Results are shown in FIG. 8. Menicon soft SiHy contact lenses were used to illustrate improved lubricity using an inclined-plane method. Menicon soft SiHy lenses were washed in milliQ, dried and treated with oxygen plasma for 60 s at 40 watts (Plasma Prep II, SPI supplies). Control lenses were incubated in 0.01 M PBS buffer (Sigma-Aldrich), two are included. In addition, freshly treated Menicon soft SiHy lenses were incubated in lipid coating composition 5 and 10 mol % (B) for 30 minutes and subsequently washed with 0.01 M PBS buffer (Sigma-Aldrich). Using an in-house build inclined-plane system (FIG. 5) lubricity improvement was shown. Here, the glass plane was cleaned in 0.1 M NaOH solution for 1 hour and rinsed with demi water. The cleaned glass plate was placed in a buffer reservoir containing 0.01 M PBS buffer (Sigma-Aldrich). One end of the glass plate was attached via a wire to a stepper motor to lift the glass plate. Here, a dynamic lubricity analysis was performed wherein the stepper motor was used to lift the glass plate at one end in time thereby increasing the angle gradually. Lenses were placed with the concave side facing the glass plate at 0 degrees. A steel ferrule of 0.5 gram was added to the lenses while the lenses. Afterwards the glass plate was slowly lifted at one end using the stepper motor at a speed of 200 hz. The experiment was recorded, and movie analysis took place using ImageJ software. Results show a similar trend compared to experiment 6-8 whereby lenses coated with lipid-coating composition have improved lubricity. Similar to the results of Experiment 6 on rigid contact lenses, the most lubricious composition on Menicon soft SiHy lenses was 10 mol % (B) followed by 5 mol % (B).

Experiment 10

Figure 9:
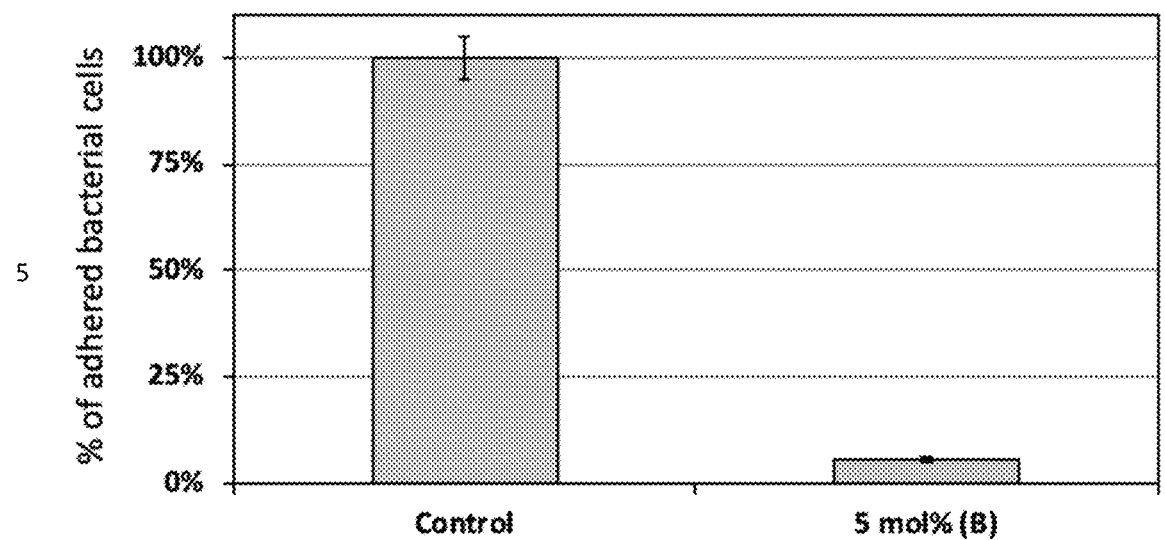
FIG. 9 shows anti-fouling for bacteria test results according to experiment 10.

Experiment 10 was performed to show the anti-fouling properties towards bacteria in stress test conditions of coated rigid contact lenses using the lipid-coating composition resulting in a lipid coating on the contact lenses. To this end, a composition from experiment 2 was used i.e. the lipid-coating composition with 5 mol % (B). Results shown in FIG. 9. Menicon Z contact lenses were used to illustrate the anti-fouling properties of the coated contact lens. The bacterial strain and ORN208 were grown overnight in LB media using tetracycline as the selective antibiotic. These were then spun down at 5000 g for 10 min and the supernatant was discarded. The bacteria were washed twice with $10 \times 10^{-3}$M HEPES, $137 \times 10^{-3}$M NaCl, pH 7 buffer by centrifugation and resuspension. Finally, the bacteria were reconstituted in this buffer and their optical density at 600 nm was measured and set to 1.0, the bacterial solution. Menicon Z contact lenses were washed in milliQ, dried and treated with oxygen plasma for 60 s at 40 watts (Plasma Prep II, SPI supplies). Control lenses incubated in 0.01 M PBS buffer (Sigma-Aldrich). In addition, freshly treated Menicon Z contact lenses were incubated in lipid coating composition 5 mol % (B) for 30 minutes and subsequently washed with 0.01 M PBS buffer (Sigma-Aldrich). The control and coated Menicon Z contact lenses were incubated for in the bacterial solution for 2 hrs. to promote bacterial fouling of the contact lenses. The lenses were subsequently washed in 0.01 M PBS buffer (Sigma-Aldrich) and stained using the Hoechst (0.1 μg/ml) DNA stain. Samples were imaged using fluorescence microscopy (Olympus IX-71) and adhered bacterial cells were counted using ImageJ software. Data is presented in FIG. 9 where the coated Menicon Z contact lenses showed a more than 95% reduction in bacterial adhesion.

Experiment 11

Figure 10:
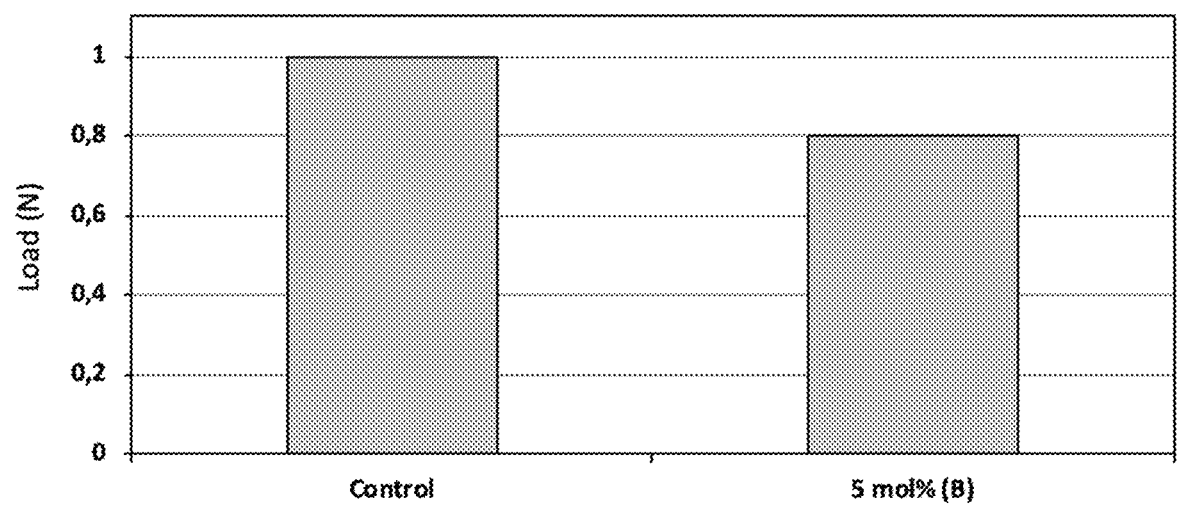
FIG. 10 shows lubricity test results according to experiment 11.

Experiment 11 was performed to show the improved lubricity of a coated catheter using the lipid-coating composition resulting in a lipid coating on the contact lenses. To this end, a composition from experiment 2 was used i.e. the lipid-coating composition with 5 mol % (B). Results shown in FIG. 10. A CVC catheter was used to illustrate the improvement in lubricity after coating. The CVC catheters were washed in milliQ, dried and treated with oxygen plasma for 60 s at 40 watts (Plasma Prep II, SPI supplies). Control CVC catheters were incubated in 0.01 M PBS buffer (Sigma-Aldrich). In addition, freshly treated CVC catheters were incubated in lipid coating composition 5 mol % (B) for 30 minutes and subsequently washed with 0.01 M PBS buffer (Sigma-Aldrich). The catheters were pulled using a load meter through a pinhole in a silicon septum. The load force was recorded after 100 cycles. A 20% reduction in required load force was observed in the coated CVC catheter samples, indicative of improved lubricity.

Experiment 12

Figure 11:
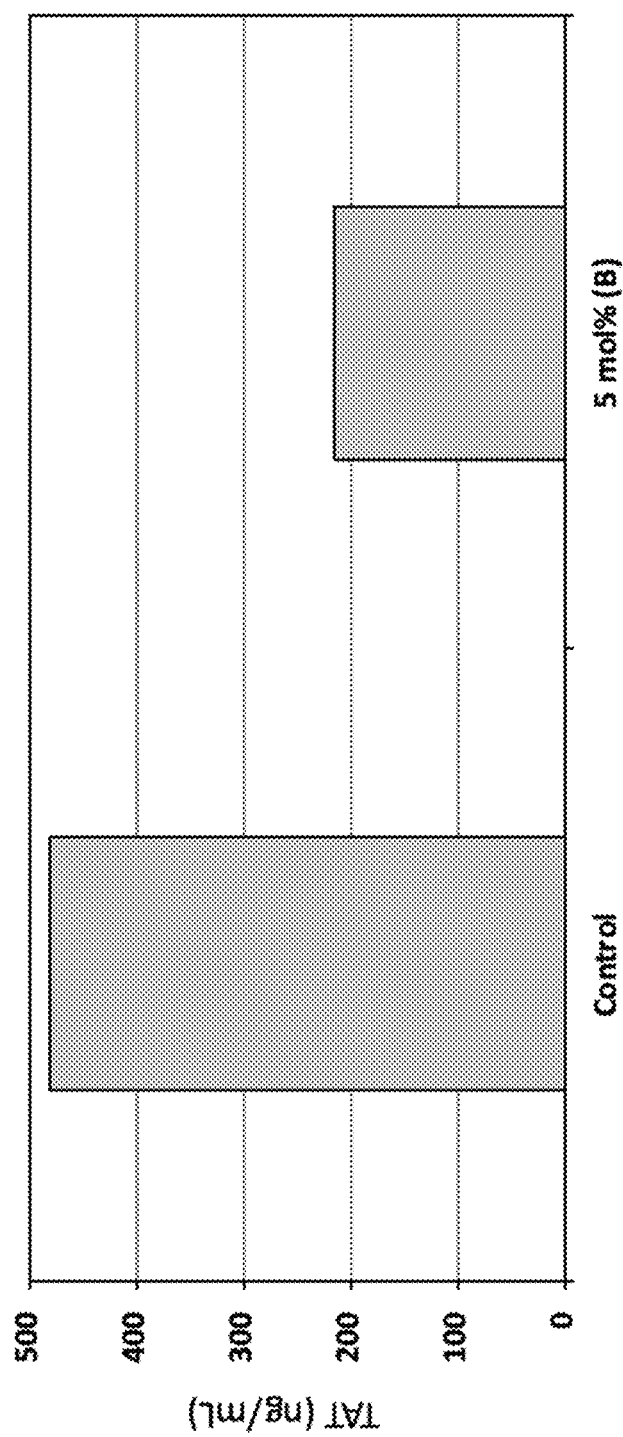
FIG. 11 shows blood compatibility test results according to experiment 12.

Experiment 12 was performed to show the improved blood compatibility of a coated catheter using the lipid-coating composition resulting in a lipid coating on the contact lenses. To this end, a composition from experiment 2 was used i.e. the lipid-coating composition with 5 mol % (B). Results shown in FIG. 11. A CVC catheter was used to illustrate the improvement in blood compatibility after coating. The CVC catheters were washed in milliQ, dried and treated with oxygen plasma for 60 s at 40 watts (Plasma Prep II, SPI supplies). Control CVC catheters were incubated in 0.01 M PBS buffer (Sigma-Aldrich). In addition, freshly treated CVC catheters were incubated in lipid coating composition 5 mol % (B) for 30 minutes and subsequently washed with 0.01 M PBS buffer (Sigma-Aldrich). The catheters were subjected to a TAT assay in a blood flow circuit to quantify the amount of Thrombin-Antithrombin-Complex (TAT). A 45% reduction in TAT complex formation was observed with the coated CVC catheter samples, indicative of improved blood compatibility.

Experiment 13 (Comparative)

Experiment 13 was performed to evaluate lipid coating formation on control surfaces using the different lipid-coating compositions and their air-stability. To this end, 4 lipid coating compositions i.e. 0.1, 0.2, 1.0 and 2.5 mol % of total lipid content of lipid (B) DSPE-PEG2000 (Avanti polar lipids) (B); and 99.7, 99.6, 98.8 and 97.3 mol % respectively of total lipid content of lipid (A) DOPC (Avanti polar lipids); and 0.2 mol % of total lipid content of lipophilic compound (C) TR-DHPE (Thermo Fisher) in ethanol (ethanol absolute ≥99.8%, VWR) were prepared at a concentration of 50 mg/ml. The aforementioned concentrate solutions were stored under argon at stored in microcentrifuge containers (R) at −20° C. for a maximum of 6 weeks. All lipids were ordered as powdered stocks and kept under argon atmosphere and stored at −20° C. for a maximum of 1 year. The concentrate solutions were dispensed into 1 mL water containing water-soluble additive (D). The water-soluble additive (D) was 0.01 M HEPES (Sigma-Aldrich), 150 mM NaCl (Sigma-Aldrich) and 2 mM CaCl2 pH (Sigma-Aldrich). The concentrate solutions were dispensed within 1 second at a dilution factor of 200 using an air-displacement P10 micropipette (Eppendorf) and subsequently agitated using a table-top vortex (labdancer, VWR) and vortexed until steady-state. The resulting lipid-coating composition had a concentration of (A)+(B)+(C) of 0.25 mg/ml containing >95 wt. % water and was characterized using dynamic light scattering (DLS, Nanotrac wave, Microtrac). The mean number-weighted diameter (Mn) of the lipid vesicles are shown in FIG. 12, lipid vesicle formation was achieved, and the solutions appeared transparent by visual observation. To study the air-stability of said compositions, 96-well glass bottoms plates (SensoPlates, Greiner Bio-one) were used and coated. The 96-well glass bottoms plates were cleaned beforehand by incubation of 300 μL 2 v/v % Hellmanex III (Sigma-Aldrich) solution in milliQ for 1 hour at room temperature and subsequently rinsed with demi water to remove the detergent. 200 μL of lipid-coating compositions were left to incubate for at least 5 minutes to form a lipid coating and subsequently washed with milliQ by means of serial dilution through addition of 100 μL of milliQ and removal of 100 μL of solution. At least 16 serial dilution were performed to remove remnants lipid-coating compositions. The glass wells were characterized using fluorescence microscopy. To this end, an Olympus inverted IX71 epi-fluorescence research microscope with a Xenon X-cite 120PC as light source and a digital Olympus DR70 camera for image acquisition was used to acquire fluorescence micrographs. TR-DHPE was imaged using $510 \leq \lambda_{ex} \leq 550$ nm and $\lambda_{em} > 590$ nm. After imaging the samples were exposed to air to demonstrate air-stability, essential for commercial use. Results shown in table 1. Successful lipid coating for formation was observed for all compositions (before drying/dehydration). None of the aforementioned lipid-based coating compositions showed improved stability and showed degradation of the coating after drying/dehydration.

|  | 0.1 mol % (B) | 0.2 mol % (B) | 1.0 mol % (B) | 2.5 mol % (B) |
|---|---|---|---|---|
| Size (DLS) nm | 74.8 | 75.1 | 94.6 | 93.5 |
| EPI before dehydration | 100% coverage | 100% coverage | 100% coverage | 100% coverage |
| EPI after dehydration | Degradation. <50% coverage | Degradation. <50% coverage | Degradation. <50% coverage | Degradation. <50% coverage |

What is claimed is:

1. A lipid-based coating composition for coating a medical device, wherein the composition comprises:
   i) lipid vesicles consisting of
      85-95 mol % of a phospholipid (A) having a phosphatidylcholine group;
      5-12 mol % of a PEGylated phospholipid (B);
      optionally 0-3 mol % of a lipophilic compound (C) other than lipids the phospholipid (A) and the PEGylated phospholipid (B);
      0-5 wt. % of a water-soluble additive (D);
   ii) at least 95 wt. % of water, and
   iii) an alcohol,
   wherein the lipid vesicles have a number average size between 50 and 140 nm measured according to dynamic light scattering,
   wherein a concentration of the lipid vesicles ranges between 0.025 mg/ml and 2 mg/ml in the composition, and
   wherein the mol % of the phospholipid (A), the PEGylated phospholipid (B) and the lipophilic compound (C) is calculated relative to the total molar amount of (A)+(B)+(C) in the composition, wherein the wt. % of water-soluble additive (D) and the wt. % of water are calculated relative to the weight of the total composition.

2. The composition according to claim 1, wherein the phospholipids (A) are chosen from 1,2-didecanoyl-sn-glycero-3-phosphocholine (DDPC), 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-Dioleoyl-sn-glycero-3-phosphocholine (DOPC), 1-palmitoyl-2-oleoyl-sn-glycero-3-phosphocholine (POPC), 1,2-dierucoyl-sn-glycero-3-phosphocholine (DEPC), a DiynePC lipid, 1,2-bis (10,12-tricosadiynoyl)-sn-glycero-3-phosphocholine and 1-palmitoyl-2-(10,12-tricosadiynoyl)-sn-glycero-3-phosphocholine.

3. The composition according to claim 2, wherein the PEGylated phospholipids (B) are chosen from the group consisting of 1,2-distearoyl-sn-glycero-3-phosphoethanolamine-N-[methoxy(polyethylene glycol)-350] (DSPE-PEG350), 1,2-distearoyl-sn-glycero-3-phosphoethanolamine-N-[methoxy(polyethylene glycol)-550] (DSPE-PEG550), 1,2-distearoyl-sn-glycero-3-phosphoethanolamine-N-[methoxy(polyethylene glycol)-750] (DSPE-PEG750), 1,2-distearoyl-sn-glycero-3-phosphoethanolamine-N-[methoxy(polyethylene glycol)-1000] (DSPE-PEG1000), 1,2-distearoyl-sn-glycero-3-phosphoethanolamine-N-[methoxy(polyethylene glycol)-2000] (DSPE-PEG2000), 1,2-distearoyl-sn-glycero-3-phosphoethanolamine-N-[methoxy(polyethylene glycol)-3000] (DSPE-PEG3000), 1,2-distearoyl-sn-glycero-3-phosphoethanolamine-N-[methoxy(polyethylene glycol)-5000] (DSPE-PEG5000), 1,2-dioleoyl-sn-glycero-3-phosphoethanolamine-N-[methoxy(polyethylene glycol)-350] (DOPE-PEG350), 1,2-dioleoyl-sn-glycero-3-phosphoethanolamine-N-[methoxy(polyethylene glycol)-550] (DOPE-PEG550), 1,2-dioleoyl-sn-glycero-3-phosphoethanolamine-N-[methoxy(polyethylene glycol)-750] (DOPE-PEG750), 1,2-dioleoyl-sn-glycero-3-phosphoethanolamine-N-[methoxy(polyethylene glycol)-1000] (DOPE-PEG1000), 1,2-dioleoyl-sn-glycero-3-phosphoethanolamine-N-[methoxy(polyethylene glycol)-2000] (DOPE-PEG2000), 1,2-dioleoyl-sn-glycero-3-phosphoethanolamine-N-[methoxy(polyethylene glycol)-3000] (DOPE-PEG3000), 1,2-dioleoyl-sn-glycero-3-phosphoethanolamine-N-[methoxy(polyethylene glycol)-5000] (DOPE-PEG5000), 1,2-dipalmitoyl-sn-glycero-3-phosphoethanolamine-N-[methoxy(polyethylene glycol)-350] (DPPE-PEG350), 1,2-dipalmitoyl-sn-glycero-3-phosphoethanolamine-N-[methoxy(polyethylene glycol)-550] (DPPE-PEG550), 1,2-dipalmitoyl-sn-glycero-3-phosphoethanolamine-N-[methoxy(polyethylene glycol)-750] (DPPE-PEG750), and 1,2-dipalmitoyl-sn-glycero-3-phosphoethanolamine-N-[methoxy(polyethylene glycol)-1000] (DPPE-PEG1000), 1,2-dipalmitoyl-sn-glycero-3-phosphoethanolamine-N-[methoxy(polyethylene glycol)-2000] (DPPE-PEG2000),
   wherein the lipophilic compound (C) is chosen from phosphatidic acid derivatives, phosphatidylglycerol derivatives, phosphatidylethanolamine derivatives, phosphatidylserine derivatives, natural phospholipid derivates, sterols, cholesterol, desmosterol, lanosterol and derivatives of sterols, polyglycerin-phospholipids, functionalized-phospholipids, terminal activated-phospholipids), N-[1-(2,3-Dioleoyloxy) propyl]-N,N,N-trimethylammonium methyl-sulfate (DOTAP), proteins, peptides, amphiphiles, ionic polymers, sugar molecules, enzymes, active pharmaceutical components and non-active pharmaceutical components, and
   wherein the water-soluble additive (D) is chosen from the group of salts, buffers, (poly) electrolytes and complexing agents.

4. The composition according to claim 1, wherein phospholipids (A) are chosen from the group consisting of 1,2-dimyristoyl-sn-glycero-3-phosphocholine (DMPC), 1,2- dipalmitoyl-sn-glycero-3-phosphocholine (DPPC), 1,2-distearoyl-sn-glycero-3-phosphocholine (DSPC), 1,2-dioleoyl-sn-glycero-3-phosphocholine (DOPC), and 1-palmitoyl-2-oleoyl-sn-glycero-3-phosphocholine (POPC).

5. The composition according to claim 4, wherein the PEGylated phospholipids (B) are chosen from the group consisting of 1,2-dipalmitoyl-sn-glycero-3-phosphoethanolamine-N-[methoxy(polyethylene glycol)-2000] (DPPE-PEG2000) and 1,2-dioleoyl-sn-glycero-3-phosphoethanolamine-N-[methoxy(polyethylene glycol)-2000] (DOPE-PEG2000),
  wherein the lipophilic compound (C) is chosen from Phosphatidic acid derivatives, Phosphatidylglycerol derivatives, Phosphatidylethanolamine derivatives, Phosphatidylserine derivatives, natural phospholipid derivates, Sterols, cholesterol, desmosterol, lanosterol and derivatives of sterols, polyglycerin-phospholipids, functionalized-phospholipids, terminal activated-phospholipids), N-[1-(2,3-Dioleoyloxy) propyl]-N, N, N-trimethylammonium methyl-sulfate (DOTAP), proteins, peptides, amphiphiles, ionic polymers, sugar molecules, enzymes, active pharmaceutical components and non-active pharmaceutical components, and
  wherein the water-soluble additive (D) is chosen from the group of salts, buffers, (poly) electrolytes and complexing agents.

6. The composition according to claim 1, wherein the phospholipids (A) are chosen from the group consisting of 1,2-dipalmitoyl-sn-glycero-3-phosphocholine (DPPC) and 1,2-dioleoyl-sn-glycero-3-phosphocholine (DOPC).

7. The composition according to claim 6, wherein the PEGylated phospholipids (B) are chosen from the group consisting of 1,2-dipalmitoyl-sn-glycero-3-phosphoethanolamine-N-[methoxy(polyethylene glycol)-2000] (DPPE-PEG2000) and 1,2-dioleoyl-sn-glycero-3-phosphoethanolamine-N-[methoxy(polyethylene glycol)-2000] (DOPE-PEG2000),
  wherein the lipophilic compound (C) is chosen from phosphatidic acid derivatives, phosphatidylglycerol derivatives, phosphatidylethanolamine derivatives, phosphatidylserine derivatives, natural phospholipid derivates, sterols, cholesterol, desmosterol, lanosterol and derivatives of sterols, polyglycerin-phospholipids, functionalized-phospholipids, terminal activated-phospholipids), N-[1-(2,3-Dioleoyloxy) propyl]-N,N,N-trimethylammonium methyl-sulfate (DOTAP), proteins, peptides, amphiphiles, ionic polymers, sugar molecules, enzymes, active pharmaceutical components and non-active pharmaceutical components, and
  wherein the water-soluble additive (D) is chosen from phosphate buffered saline (PBS), HEPES, $NaCl_2$ and $CaCl_2$).

8. The composition according to claim 1, wherein the PEGylated phospholipids (B) are chosen from the group consisting of 1,2-distearoyl-sn-glycero-3-phosphoethanolamine-N-[methoxy(polyethylene glycol)-350] (DSPE-PEG350), 1,2-distearoyl-sn-glycero-3-phosphoethanolamine-N-[methoxy(polyethylene glycol)-550] (DSPE-PEG550), 1,2-distearoyl-sn-glycero-3-phosphoethanolamine-N-[methoxy(polyethylene glycol)-750] (DSPE-PEG750), 1,2-distearoyl-sn-glycero-3-phosphoethanolamine-N-[methoxy(polyethylene glycol)-1000] (DSPE-PEG1000), 1,2-distearoyl-sn-glycero-3-phosphoethanolamine-N-[methoxy(polyethylene glycol)-2000] (DSPE-PEG2000), 1,2-distearoyl-sn-glycero-3-phosphoethanolamine-N-[methoxy(polyethylene glycol)-3000] (DSPE-PEG3000), 1,2-distearoyl-sn-glycero-3-phosphoethanolamine-N-[methoxy(polyethylene glycol)-5000] (DSPE-PEG5000), 1,2-dioleoyl-sn-glycero-3-phosphoethanolamine-N-[methoxy(polyethylene glycol)-350] (DOPE-PEG350), 1,2-dioleoyl-sn-glycero-3-phosphoethanolamine-N-[methoxy(polyethylene glycol)-550] (DOPE-PEG550), 1,2-dioleoyl-sn-glycero-3-phosphoethanolamine-N-[methoxy(polyethylene glycol)-750] (DOPE-PEG750), 1,2-dioleoyl-sn-glycero-3-phosphoethanolamine-N-[methoxy(polyethylene glycol)-1000] (DOPE-PEG1000), 1,2-dioleoyl-sn-glycero-3-phosphoethanolamine-N-[methoxy(polyethylene glycol)-2000] (DOPE-PEG2000), 1,2-dioleoyl-sn-glycero-3-phosphoethanolamine-N-[methoxy(polyethylene glycol)-3000] (DOPE-PEG3000), 1,2-dioleoyl-sn-glycero-3-phosphoethanolamine-N-[methoxy(polyethylene glycol)-5000] (DOPE-PEG5000), 1,2-dipalmitoyl-sn-glycero-3-phosphoethanolamine-N-[methoxy(polyethylene glycol)-350] (DPPE-PEG350), 1,2-dipalmitoyl-sn-glycero-3-phosphoethanolamine-N-[methoxy(polyethylene glycol)-550] (DPPE-PEG550), 1,2-dipalmitoyl-sn-glycero-3-phosphoethanolamine-N-[methoxy(polyethylene glycol)-750] (DPPE-PEG750), 1,2-dipalmitoyl-sn-glycero-3-phosphoethanolamine-N-[methoxy(polyethylene glycol)-1000] (DPPE-PEG1000), and 1,2-dipalmitoyl-sn-glycero-3-phosphoethanolamine-N-[methoxy(polyethylene glycol)-2000] (DPPE-PEG2000).

9. The composition according to claim 1, wherein the PEGylated phospholipids (B) are chosen from the group consisting of 1,2-dipalmitoyl-sn-glycero-3-phosphoethanolamine-N-[methoxy(polyethylene glycol)-2000] (DPPE-PEG2000) and 1,2-dioleoyl-sn-glycero-3-phosphoethanolamine-N-[methoxy(polyethylene glycol)-2000] (DOPE-PEG2000).

10. The composition according to claim 1, wherein the lipophilic compound (C) is chosen from phosphatidic acid derivatives, phosphatidylglycerol derivatives, phosphatidylethanolamine derivatives, phosphatidylserine derivatives, natural phospholipid derivates, sterols, cholesterol, desmosterol, lanosterol and derivatives of sterols, polyglycerin-phospholipids, functionalized-phospholipids, terminal activated-phospholipids, N-[1-(2,3-Dioleoyloxy) propyl]-N,N, N-trimethylammonium methyl-sulfate (DOTAP), proteins, peptides, amphiphiles, ionic polymers, sugar molecules, enzymes, active pharmaceutical components and non-active pharmaceutical components.

11. The composition according to claim 1, wherein the water-soluble additive (D) is chosen from the group of salts, buffers, (poly) electrolytes and complexing agents.

12. A medical device comprising the composition according to claim 1, wherein the medical device is a contact lens, a catheter, or a medical implant.

13. A medical device comprising the composition according to claim 3, wherein the medical device is a contact lens, a catheter, or a medical implant.

14. The composition according to claim 1, wherein the alcohol is ethanol.

15. A method, comprising the step of:
  applying the composition of claim 1 on a substrate or repairing defects in a lipid on a substrate with the coating composition of claim 1.

* * * * *

UNITED STATES PATENT AND TRADEMARK OFFICE
CERTIFICATE OF CORRECTION

| | | |
|---|---|---|
| PATENT NO. | : 12,194,146 B2 | Page 1 of 1 |
| APPLICATION NO. | : 16/975826 | |
| DATED | : January 14, 2025 | |
| INVENTOR(S) | : Jasper Van Weerd | |

It is certified that error appears in the above-identified patent and that said Letters Patent is hereby corrected as shown below:

In the Claims

In Claim 3, Column 16, Line 57, after the word "pholipids" delete ")".

In Claim 5, Column 17, Line 19, after the word "pholipids" delete ")".

In Claim 7, Column 17, Line 45, after the word "pholipids" delete ")".

In Claim 15, Column 18, Line 63, delete "coating".

Signed and Sealed this
Eighth Day of April, 2025

Coke Morgan Stewart
*Acting Director of the United States Patent and Trademark Office*